United States Patent [19]

Baldi et al.

[11] 4,099,006
[45] Jul. 4, 1978

[54] PROCESS FOR THE PRODUCTION OF CHLORO-AMINO-S-TRIAZINES

[75] Inventors: Luciano Baldi, Turin; Corrado Ferrari, Parma; Renato Francese, Turin, all of Italy

[73] Assignee: Rumianca S.p.A., Turin, Italy

[21] Appl. No.: 645,137

[22] Filed: Dec. 29, 1975

[30] Foreign Application Priority Data

Jan. 3, 1975 [IT] Italy .................................. 67013 A/75

[51] Int. Cl.² .................. C07D 251/44; C07D 251/50
[52] U.S. Cl. ...................................... 544/204; 544/194
[58] Field of Search .......................... 260/249.5, 249.8; 544/194, 204

[56] References Cited

U.S. PATENT DOCUMENTS

| | | | |
|---|---|---|---|
| 3,639,399 | 2/1972 | Daugherty et al. | 260/249.5 |
| 3,681,335 | 8/1972 | Saul et al. | 260/249.8 |
| 4,054,739 | 10/1977 | Haschke et al. | 544/204 |
| 4,058,662 | 11/1977 | Haschke et al. | 544/204 |

*Primary Examiner*—John M. Ford
*Attorney, Agent, or Firm*—Sughrue, Rothwell, Mion, Zinn and Macpeak

[57] ABSTRACT

2-chloro-s-triazine substituted in at least one of the positions 4,6 of the triazine ring with an amino group is obtained by feeding separately an aqueous amine solution and an aqueous NaOH solution into a water-organic liquid reaction medium containing cyanuric chloride, delivering to said medium per unit of time from 1.05 to 1.30 moles of amine for each mole of sodium hydroxide, feeding the amine solution until an amount of from 1 to 2 moles of amine per mole of cyanuric chloride is reached in the medium and the NaOH solution until an amount in moles equal to or slightly higher than the amount of amine moles fed in is reached in the medium. The temperature of the reaction medium is maintained at a value of from 5°–15° C to 60°–70° C during the feeding period.

15 Claims, No Drawings

PROCESS FOR THE PRODUCTION OF CHLORO-AMINO-S-TRIAZINES

The present invention concerns a process for the production of chloro-amino-s-triazines, in particular of 2-chloro-s-triazine substituted in at least one of the two positions 4 and 6 of the triazine nucleus with an amino group.

As known these compounds constitute a very important group of herbicides, also, contemporaneously, intermediate products useful for the production of other herbicides, pesticides, dyes, active bleaching agents and other substances.

Therefore, particular attention has been dedicated, in the art, to the development of simple and economic processes for obtaining such compounds, with a high yield and purity.

The preparation of such compounds starting from cyanuric chloride and amines in the presence of an acceptor of acids, is already known in the art, (for example: W. Pearlman and C. K. Banks: J. Am. Chem. Soc., 70, 3726, 1948), and is one of the ones most followed.

A number of methods have been proposed in the art for obtaining from cyanuric chloride and amine 2-chloro-s-triazine substituted in at least one of the positions 4 and 6 of the triazine nucleus with an amino group, and they differentiate above all for the medium wherein the reaction is carried out.

Thus the reaction may be effected in water, wherein suitable surface-active agents have been added, in order to have a good suspension of the finely subdivided cyanuric chloride. However this procedure is not utilizable on an industrial scale, since the velocities of reaction are too slow.

Recourse may also be made to an aqueous monophase medium, such as water/acetone, or water/dioxane, wherein the organic solvent in which the cyanuric chloride is soluble, is completely miscible with water. However such a medium presents some not negligible drawbacks due, above all, to the formation of undesired products, such as triamino-s-triazine and hydrolysis products which decrease noticeably the yield in desired product.

Moreover the recovery of the desired product from such reaction mixtures is quite involved and uneconomic.

Another drawback stems from the fact that the final recovery of the solvent is incomplete and that this increases further the cost of the process.

Finally to avoid the formation of undesired products due to the hydrolysis, very low temperatures, lower than 0° and down to −15° C are required, a fact which industrially creates not negligible problems.

Recourse can again be made to an aqueous biphase medium, such as water/carbon tetrachloride, water/toluene or water/chlorobenzene, wherein the organic solvent in which the cyanuric chloride is soluble, is practically immiscible with water.

However even such a procedure is of scarce interest on an industrial scale, above all because the velocities of reaction are too slow.

Aqueous biphase systems, such as water/methyl ethyl ketone, water/methyl propyl ketone or water/diethyl ketone, wherein the organic solvent, in which the cyanuric chloride is soluble, is partially soluble in water have also been proposed.

As in all the other mediums comprising water, even in this case, the reaction between cyanuric chloride and amine must be effected at rather low temperatures, always lower than 0° C, in order to avoid the hydrolysis of cyanuric chloride, which would be conducive to the presence of contaminative products of difficult and expensive separation.

This fact involves a number of difficulties, due to the exothermic nature of the reaction and the consequent danger of local overheating, and therefore of undesired side reactions, as well as the technical complications for the maintenance of such conditions.

In particular, on account of the difficulty of maintaining by simple outside cooling, homogeneous temperature conditions within the reactor, it might be necessary to proceed straight to the addition of ice within the reaction medium.

This fact, however, has rather negative repercussions on the simplicity and economy of the process.

Furthermore, whenever recourse is made to a solvent partially miscible with water, it is not easy to recover the solvent in an anhydrous form for an economic recycling of the same.

On the other hand the use of non aqueous mediums for the reaction of cyanuric chloride with the amines, for instance the use of carbon tetrachloride, toluene or chlorobenzene, even if suggested in the literature, has not found a practical industrial application.

A new process has now been found for the production of 2-chloro-s-triazines substituted in at least one of the positions 4 and 6 of the triazine ring with an amino group, which allows the drawbacks of the prior art to be overcome in a simple and economically advantageous way.

Thus, the invention provides a process for the production of 2-chloro-s-triazine substituted in at least one of the positions 4,6 of the triazine ring with an amino group, by reaction in a water-organic liquid medium between cyanuric chloride and an amine in the presence of sodium hydroxide, characterized by:

feeding contemporaneously and separately an aqueous solution of a primary or secondary amine and an aqueous solution of sodium hydroxide into a reaction medium containing a solution of cyanuric chloride in an organic liquid immiscible or partially miscible with water, having a boiling point of from 60° to 130° C, adjusting the feed rate of the amine and sodium hydroxide solutions so as to feed per unit of time from 1.05 to 1.30 moles of amine for each mole of sodium hydroxide;

stopping the feeding of the amine solution when an amount of from 1 to 2 moles of amine per mole of cyanuric chloride is reached in the reaction medium;

stopping the feeding of the sodium hydroxide solution when an amount of sodium hydroxide moles equal to or slightly higher than the amount of amine moles fed in is reached in the reaction medium;

maintaining during the feeding period the temperature of the reaction mixture at a value of from 5°–15° C to 60°–70° C; and recovering the resulting substituted 2-chloro-s-triazine from the reaction medium.

Feeding contemporaneously and separately the two solutions, while maintaining a lower feed rate of the hydroxide, constitutes one of the fundamental aspect of the process of the invention.

Maintaining the feed rate of the amine from 1.05 to 1.30 times the feed rate of NaOH, until an amount of from 1 to 2 moles of amine per mole of cyanuric chloride is reached in the reaction medium, constitutes another of the essential aspects of the present invention.

Continuing the feed of the NaOH solution, once the feed of the amine solution is terminated, until an amount in moles of NaOH equal to or slightly higher than the amount of amine moles fed in is reached in the reaction medium, constitutes another of the essential aspects of the process of the present invention. Generally, the amount in moles of NaOH does not exceed by more than 5% the amount of amine moles fed in.

Effecting the reaction between cyanuric chloride and amine at a temperature ranging from 5°–15° to 60°–70° C, while obtaining for the end product very high yields and purity, constitutes another of the essential aspects of the process of the present invention.

The last one is the most surprising aspect of the process of the invention, because on the basis of the known art, it would not be possible to exceed for the reaction under question, in a water-organic liquid medium, especially in the initial part, a temperature of 0°–5° C without hydrolysis reactions which lower the yield and cause the formation of undesirable side products which cannot be separated without involved procedures.

According to the process of the present invention, not only the undesired phenomena of hydrolysis are practically absent, even at temperature higher than 0° C, but the reaction is carried out at temperature values that can be easily controlled, contrarily to the low temperature technique of the prior art.

The process according to the present invention is advantageously applied to the preparation of 2-chloro-s-triazine substituted in the positions 4 and 6 of the triazine ring with two amino groups.

When it is desired to fix two identical amino groups in the positions 4 and 6 of the triazine ring of the 2-chloro-s-triazine, the operation is carried out essentially as hereinbefore indicated.

When it is desired to fix two different amino groups in the positions 4 and 6 of the triazine ring, the procedure is modified by:

feeding contemporaneously and separately in a first reaction stage an aqueous solution of a first amine and an aqueous solution of sodium hydroxide into the said reaction medium;

adjusting the feed rate of the said first amine and sodium hydroxide solutions so as to feed per unit of time from 1.05 to 1.30 moles of said first amine for each mole of sodium hydroxide;

stopping the feeding of said first amine solution when an amount of 1 mole of amine per mole of cyanuric acid is reached in the reaction medium;

stopping the feeding of the sodium hydroxide solution when an amount of NaOH moles equal to or slightly higher than the amount of amine moles fed in is reached in the reaction medium;

maintaining during the feed period the temperature of the reaction medium at a value of from 5°–15° to 20°–25° C;

bringing the pH of the reaction medium to a value lower than 4 and recovering from said reaction medium the organic phase containing the resulting 2,4-dichloro-6-amino-s-triazine;

feeding contemporaneously and separately in a second reaction stage an aqueous solution of a second and different amine and an aqueous solution of sodium hydroxide into the said recovered organic phase;

adjusting the feed rate of the said second amine and sodium hydroxide solutions so as to feed per unit of time from 1.05 to 1.30 moles of said second amine for each mole of sodium hydroxide;

stopping the feeding of said second amine solution when an amount of 1 mole of said second amine per mole of 2,4-dichloro-6-amino-s-triazine is reached in the reaction medium;

stopping the feeding of the sodium hydroxide solution when an amount of sodium hydroxide moles equal to or slightly higher than the amount of second amine moles fed in is reached in the reaction medium;

maintaining during the feed period the temperature of the reaction medium at a value of from 20°–25° C to 60°–70° C; and recovery from the reaction medium the resulting 2-chloro-s-triazine substituted in the positions 4 and 6 with two different amino groups.

The adjustment of the pH of the reaction medium to a value lower than 4 and preferably from 2 to 3 and the subsequent separation of the aqueous layer from the organic one at the end of the first stage, constitutes an essential aspect of this embodiment, because it clearly affects the purity of the end product. In effect, traces of the amine used in the first stage which did not react completely with the cyanuric chloride are present in the aqueous layer. By eliminating this amine one avoids that the same could react in the second stage with the intermediate 2,4-dichloro-6-amino-s-triazine to form the undesirable symmetrical product.

A plurality of amines are utilizable in the process of the present invention, varying according to the nature of the desired product, that is a herbicide, or an intermediate for other products such as various pesticides, dyes, activated bleaching agents and others.

Generally, in the case of herbicides, aliphatic amines with a small number of carbon atoms, or alicyclic-, or aromatic amines or other substituted amines, such as methylamine, ethylamine, propylamine, isopropylamine, dimethylamine, n-butylamine, sec-butylamine, tert-butylamine, cyclohexylamine, γ-methoxypropylamine, β-ethoxymethylamine, ethanolamine, are used.

The process according to the present invention, for instance, may be advantageously applied to the preparation of:

2-chloro-4,6-bis(ethylamino)-s-triazine
2-chloro-4,6-bis(isopropylamino)-s-triazine
2-chloro-4-ethylamino-6-isopropylamino-s-triazine
2-chloro-4-ethylamino-6-diethylamino-s-triazine
2-chloro-4-ethylamino-6-tert-butylamino-s-triazine utilizing as amines: ethylamine, isopropylamine, tert-butylamine and diethylamine.

The organic liquid may be chosen among a large number of organic compounds solvent for cyanuric chloride and having the required characteristics hereinbefore indicated. Preferred organic compounds for the purpose are toluene, chlorobenzene and carbon tetrachloride among those non-miscible with water, and methyl ethyl ketone, methyl propyl ketone and diethyl ketone among those partially miscible with water.

Conveniently, the amount of water in the said water-organic liquid medium containing cyanuric chloride, should not exceed 50% by weight and preferably should be from 20 to 30% by weight, with respect to the weight of the water-liquid organic mixture.

Once the feed of the amine solution is terminated, the feed of the sodium hydroxides is generally continued until one reaches in the reaction medium an amount in moles of NaOH of from the amount of amine moles fed in to an excess of 5% with respect to the latter, and preferably until said amount in moles of NaOH is in excess of from 2 to 4% with respect to the amount of amine moles fed in.

Once the feed of the amine and sodium hydroxide solutions has been terminated, the temperature is preferably maintained at the value reached at the end of the feeding for a period of at least 5 minutes in order to complete the reaction. A period exceeding 15 minutes does not bring any appreciable advantages for the purposes of the invention.

The recovery of the substituted 2-chloro-s-triazine may be effected by any one of the known separation techniques.

In an advantageous embodiment, when an organic liquid capable of forming a low boiling azeotrope with water is used, first the organic liquid present is removed from the reaction medium, generally after dilution with water, by azeotropic distillation with water, and subsequently, the substituted 2-chloro-s-triazine, suspended in the residual solution, is separated, for example, by filtration or centrifugation.

In some cases it may be advantageous to add, before carrying out the organic liquid distillation, small amounts of a wetting agent, such as, for instance, lignin sulfonate, in order to avoid the formation of agglomerated products.

In another advantageous embodiment, the dilution of the reaction medium with water, which may contains small amounts of wetting agent, is first performed and subsequently the substituted 2-chloro-s-triazine suspended in the resulting medium is separated, for example, by filtration or by centrifugation.

With respect to the processes already known in the art for the preparation of 2-chloro-s-triazines, the process according to the present invention offers many advantages.

Operating according to the process of the present invention, besides the aforesaid drawbacks, the necessity of a careful control of the pH during the addition of sodium hydroxide is also avoided.

Other advantages derive from the high yields and also the high purity of the end product and from the possibility of reducing the volumes involved and consequently from the utilization of reactors of reduced size.

The invention will now be illustrated by the following Examples which, however, do not intend to limit its scope in any way.

EXAMPLE 1

A 2 liters glass reactor, supplied with a stirrer, a thermometer and two separated inlets for the feed of the reagents has been used. This reactor was cooled on the outside by brine circulation.

About 184 g (1 mole) of cyanuric chloride have been initially dissolved in about 500 g of toluene (B.P. 110.6° C) in this reactor.

As soon as the temperature of the mixture has been stabilized at +5° C, 84 g of isopropylamine aqueous solution (isopropylamine concentration: 70 wt.%, 1 mole of isopropylamine) and 134 g of a sodium hydroxide aqueous solution NaOH concentration: 30 wt.%., 1 mole of NaOH have been added under vigorous stirring.

The addition of the two solutions has been effected at the same time but separately through the two inlets of the reactor.

Furthermore the two velocities of feed have been controlled in such a way that the addition of isopropylamine solution would be terminated in 25', while that of the sodium hydroxide solution would be terminated in 28'. In other words the velocity of the feed of the isopropylamine has been 1.12 times that of the sodium hydroxide.

During the addition the temperature increased from +5 to 20°-22° C while the pH from an initial value of 2-3 increased to a maximum value of 9.5 to decrease afterwards to 6-7.

When the addition has been terminated, the mixture has been kept under reaction for 10 minutes longer at 20° C. Subsequently 200 g of dilute hydrochloric acid (0.1% by weight) have been added so as to bring the pH of the reaction medium to a value of about 2-3, the mixture has been stirred for 15', then the stirring has been arrested, the mixture has been allowed to decant and the aqueous layer has been discharged.

Then about 90 g of an ethylamine aqueous solution (1 mole of ethylamine, ethylamine concentration: 50 wt.%) and about 138 g of a sodium hydroxide aqueous solution (1.03 moles of NaOH, NaOH concentration: 50 wt.%) have been added under vigorous stirring, to the 2,4-dichloro-6-isopropylamine-s-triazine toluene solution remaining in the reactor.

This second addition too has been made contemporaneously and separately, with the same procedure followed during the first addition.

During this second addition the temperature raised from 25° to 60° C, while the pH reached at the end, the value of 11.

After these conditions have been maintained for 10', during which the reaction went to completion, 500 ml of water, containing 1 g of aluminum lignin sulfonate as wetting agent have been added and the mass has been submitted to distillation at 100° C in such a way as to eliminate the toluene in the form of toluene/water azeotrope (B.P. 85° C).

750 ml more water have been added to the distillation residue and the suspension obtained has been filtered at 60° C.

The separated solid has been washed until complete elimination of the sodium chloride. After drying in an oven at 100° C, 206 g of 2-chloro-4-ethylamino-6-isopropylamino-s-triazine (atrazine) have been obtained, with a yield, as referred to cyanuric chloride, equal to 96% and a purity of about 99%.

EXAMPLE 2

In a reactor similar to that of Example 1, about 184 g (1 mole) of cyanuric chloride have been dissolved in 750 ml of carbon tetrachloride (B.P. 76.5° C), operating at room temperature.

About 84 g of an isopropylamine aqueous solution (1 mole of isopropylamine, isopropylamine content: 70 wt.%) and about 134 g of a sodium hydroxide aqueous solution (1 mole of NaOH, NaOH content: 30 wt.%) have been added under vigorous stirring, while cooling by water circulation in the jacket.

The other operations as described in Example 1 have been then exactly repeated. During the reaction between isopropylamine and cyanuric chloride the temperature has been maintained at around 20°–25° C.

10–15' after completion of the addition of ethylamine, during which the temperature varied from 20° to 55° C, 750 ml of water have been added and the mass has been submitted to distillation of 70° C in such a way as to distil off a carbon tetrachloride/water azeotrope (B.P. 66° C, composition: 96% $CCl_4$).

After completion of the same operations as in Example 1, 206 g of atrazine of a purity higher than 98% have been obtained with a yield of about 96%.

EXAMPLE 3

Example 1 has been repeated with the same reagents and the same relative amounts and substantially with the same operative procedure, with the exception that the cooling of the reactor has been obtained by means of running water circulating in the reactor jacket.

During the reaction between cyanuric chloride and isopropylamine the temperature has been maintained at 20°–25° C, while during the ethylamine addition it has been allowed to rise from 20° to about 55° C.

Besides, during the addition of the isopropylamine solution and of the ethylamine solution, the feed velocities of the amines have been controlled so that they would be equal to 1.2 times that of the sodium hydroxide.

204 g of atrazine of 98% purity, with a yield equal to about 95% have been obtained.

EXAMPLE 4

A stainless steel 100 liters autoclave with a stirrer and a thermometer, two separate inlets for the feed of the reagents and an external cooling jacket was used.

Initially about 8 kg (about 43.4 moles) of cyanuric chloride have been dissolved at room temperature in about 25 kg of toluene in the autoclave.

The mass has been cooled by means of brine circulation in the jacket and the autoclave has been fed under vigorous stirring, with about 3.66 kg of isopropylamine aqueous solution (about 43.4 moles of isopropylamine, isopropylamine content: 70 wt.%) and about 5.84 kg of sodium hydroxide aqueous solution. (NaOH content: 30 wt.%, about 43.8 moles of NaOH, that is an excess of about 1% with respect to the feed in isopropylamine).

The addition of the two solutions has been effected contemporaneously but separately, through the two inlets of the autoclave.

Moreover the velocities of the two feedings have been regulated in such a way that the addition of the isopropylamine solution would be terminated in 45' while that of sodium hydroxide solution would be terminated in 49'.

Thus the velocity of feed of the isopropylamine has been equal to 1.09 times that of the sodium hydroxide.

The conditions have been controlled so as to maintain the temperature between 20° and 25° C.

When the addition has been terminated, the mixture has been maintained in reaction for 15' longer at 20° C.

Subsequently 7 liters of dilute hydrochloric acid (0.1% by weight) have been added in such a manner as to bring the pH of the reaction medium to a value of about 2–3. After 15', the stirrer has been arrested, the solution has been allowed to decant and the aqueous layer has been discharged.

To the 2,4-dichloro-6-isopropylamino-s-triazine toluene solution remaining in the autoclave, about 3.90 kg of an ethylamine aqueous solution (about 43.4 moles of ethylamine, ethylamine content of 50 wt.%) and about 6.00 kg of a sodium hydroxide aqueous solution (NaOH content: 30 wt.%, about 45 moles of NaOH, that is an excess of about 3.7% with respect to the feed in ethylamine), have been added under vigorous stirring.

This second addition has also been made contemporaneously in a separate way with the same procedure followed during the first addition, allowing the temperature to rise from 20°–25° C to 65° C.

After 10–15', during which the reaction has been completed, the mass has been cooled and 20 liters of water containing 40 g of aluminum lignin sulfonate have been added.

The suspension obtained has been centrifugated and the separated product, after washing until elimination of the sodium chloride, has been dried in an oven at 110° C for 10 hours. 9.0 kg of atrazine of purity higher than 98% have been obtained with a yield equal to 94%.

The toluene separated from the water by decantation could still be used again and recycled.

EXAMPLE 5

About 10 kg (about 54.2 moles) of cyanuric chloride have been dissolved in an autoclave as in Example 4, at room temperature in 30 kg of methyl ethyl ketone (B.P. 79.6° C).

4.56 kg of an isopropylamine aqueous solution (about 54.1 moles of isopropylamine, isopropylamine content: 70 wt.%) and about 7.2 kg of a sodium hydroxide aqueous solution (about 54.1 moles of NaOH, NaOH content: 30 wt.%) have been added under vigorous stirring.

The addition of the two solutions has been effected at the same time, but separately so that the addition of the isopropylamine solution would be terminated in 21' while that of the sodium hydroxide in 25'. In this way the velocity of feed of the isopropylamine has been equal to 1.19 times that of the sodium hydroxide.

The conditions have been controlled in such a way as to maintain the temperature between 20° and 25° C.

After the addition has been terminated, the mixture has been maintained in reaction for 15' longer at 25° C. Subsequently 8 liters of dilute hydrochloric acid (0.1% by weight) have been added so as to bring the pH of the reaction medium to a value of 2–3. After about 15', the stirrer was arrested, the solution has been allowed to decant and the aqueous layer has been discharged.

About 4.88 kg of an ethylamine aqueous solution (about 54.1 moles of ethylamine, ethylamine content: 50 wt.%) and about 7.5 kg of a sodium hydroxide aqueous solution (NaOH content: 30 wt.%, 56.2 moles of NaOH, that is an excess of about 3.8% with respect to the feed in ehylamine), have been added under vigorous stirring to the solution remaining in the autoclave, according to the procedure followed in the first addition and allowing the temperature to rise from 20°–25° C to 65° C.

After 15', 20 liters of water have been added and the mass has been submitted to distillation at 100° C so as to distil off the water/methyl ethyl ketone azeotrope (distillation range 75°–99° C).

The suspension obtained has been centrifugated and the separated product, after washing until elimination of the sodium chloride, has been dried in an oven at 100° C for 10 hours.

11.1 kg of atrazine have been obtained (yield 96% with a purity higher than 98%).

EXAMPLE 6

In a 2 liters glass reactor similar to that of Example 1, cooled with brine, the run of Example 1 has been exactly repeated, substituting the toluene with the same amount of methyl ethyl ketone and maintaining the other conditions unchanged. Thus the temperature of the first step (cyanuric chloride reaction with isopropylamine) has been allowed to rise from the initial +5° C to 20°–22° C and maintained at this level, after completion of the addition, for 15′ minutes longer, while in the second step (ethylamine reaction) the temperature has been allowed to rise up to 60° C.

The final reaction product has been submitted to distillation at 100° C in such a manner as to remove the water/methyl ethyl ketone azeotrope (distillation range: 75°–99° C).

750 g of water have been added to the residue and the suspension has been filtered at 60° C.

The solid thus recovered has been washed until elimination of the sodium chloride and has been dried in an oven at 100° C for 10 hours.

206 g of atrazine of a purity equal to 99% and with a yield, referred to the cyanuric chloride, equal to 96% have been obtained.

EXAMPLE 7

The run of Example 1 has been repeated, introducing, however, 184 g of cyanuric chloride in a medium consisting of 750 ml of toluene and 500 ml of water. The reactor has been cooled by means of brine circulation in the external jacket.

As soon as the temperature of the mixture has been stabilized at 20° C, isopropylamine and sodium hydroxide have been added in amounts and under conditions similar to those of Example 1.

When the addition has been terminated, the mixture has been allowed to react for 15′ minutes longer at 25° C under stirring.

Subsequently, 100 g of dilute hydrochloric acid (0.1% by weight) have been added so as to bring the pH of the reaction medium to a value of about 2–3, the mass has been stirred for 15′, then the stirrer has been arrested, the mixture has been allowed to decant and the aqueous layer has been discharged.

Ethylamine and sodium hydroxide have been added to the intermediate solution in amounts and under conditions still similar to those of Example 1.

The temperature rose from 20° to 55° C. When the addition has been terminated, the reaction mixture has been maintained for 10–15′ longer at 55° C.

Subsequently 750 ml of water have been added and the mass has been submitted to distillation at 100° C in such a manner as to remove the toluene in the form of a toluene/water azeotrope (B.P. 85° C).

The residual aqueous suspension has been filtered at 60° C and the separated solid has been washed until complete elimination of the sodium chloride.

After drying for 10 hours in an oven at 100° C, 204 g of atrazine have been obtained with a yield on the cyanuric chloride equal to 95% and a purity equal to 98.5%.

EXAMPLE 8

184 g of cyanuric chloride and 590 g of toluene have been introduced in this order, in a 2 liter glass reactor cooled by brine as in Example 1.

As soon as the temperature of the mixture has been stabilized at +5° C, 180 g of an ethylamine aqueous solution at 50 wt.% and 272 g of a sodium hydroxide aqueous solution at 30 wt.% have been separately added under vigorous stirring.

The addition of the two solutions has been effected contemporaneously but controlling the velocity of the two feedings in such a way that the addition of the ethylamine solution would be terminated in 20′ while that of the sodium hydroxide solution would be terminated in 28′. In other words the velocity of the feed of the ethylamine was equal to 1.25 times that of the sodium hydroxide.

During the addition the temperature rose from +5° C to 52° C (at 20° C the brine has been discharged) while the pH at the end reached a value of 10–11.

Then 750 ml of water have been added, the mass has been cooled at 20° C and the suspension has been filtered.

The solid thus recovered has been washed until elimination of the sodium chloride. After drying for 10 hours in an oven at 100° C, 196 g of 2-chloro-4,6-bis-ethylamino-s-triazine (simazine) have been obtained with a yield, referred to the cyanuric chloride, of 97% and a purity higher than 99%.

EXAMPLE 9

As in Example 1 about 184 g of cyanuric chloride have been dissolved in 590 g of methyl ethyl ketone in a 2 liter glass reactor.

As soon as the temperature of the mixture has been stabilized at +5° C, 136 g of an aqueous solution containing 33 wt.% of ethylamine and 134 g of a sodium hydroxide aqueous solution (30 wt.% of NaOH) have been added under vigorous stirring.

The addition of the two solutions have been effected contemporaneously but separately, and regulating the velocities of the feeds in such a manner that the addition of the ethylamine solution would be terminated in 25′ while that of the sodium hydroxide solution would be terminated in 28′ (velocities ratio of 1.12:1).

During the addition the temperature rose at 20°–22° C, while the pH, from an initial value of 2–3 rose to a maximum value of 9.5 to decrease thereafter at 6.

After completion of the addition, the mixture was kept under reaction for 10′ longer at 20° C. Subsequently 200 ml of dilute hydrochloric acid (0.1 wt.%), have been added so as to bring the pH to about 2, the stirring has been maintained for 15′ longer, then it has been arrested, the mixture has been allowed to decant and the aqueous layer has been discharged.

105 g of aqueous solution containing 70 wt.% of diethylamine and 138 g of a sodium hydroxide aqueous solution (30 wt.% of NaOH), have been added, under vigorous stirring, to the intermediate solution remaining in the reactor.

This addition also has been made contemporaneously and separately in the same manner as in the first addition.

During this second addition the temperature rose from 25° to about 60° C, while the pH reached at the end a value of 11.

The final reaction product has been submitted to distillation at 100° C, in such a way as to remove the water/methyl ethyl ketone azeotrope (distillation range 75°–99° C).

750 g of water have been added to the residue, and the latter has then been cooled to 20° C and the resulting suspension has been filtered. The solid thus obtained has been washed until elimination of the sodium chloride and then has been dried in an oven at 80° for 10 hours.

220 g of 2-chloro-4-ethylamino-6-diethylamino-s-triazine (trietazine) have been obtained with a yield of 96% referred to the cyanuric chloride and a purity equal to 98%.

EXAMPLE 10

The operation was carried out according to the procedure of Example 9, with the exception of the feed in the first step of 84 g of a 33 wt.% ethylamine aqueous solution and in the second step by substituting for the diethylamine, 105 g of a 70 wt.% tert-butylamino aqueous solution.

At the end, 220 g of 2-chloro-4-ethylamino-6-tert-butylamino-s-triazine have been obtained, with a yield of 96%, referred to the cyanuric chloride and a purity of the product equal to 98%.

EXAMPLE 11

As in Example 1, 184 g of cyanuric chloride have been dissolved in 500 g of toluene in a reactor cooled by brine.

As soon as the temperature has been stablized at +5° C, 169 g of a 70 wt.% isopropylamine aqueous solution and 272 g of a 30 wt.% sodium hydroxide aqueous solution have been added under vigorous stirring.

The addition of the two solutions has been made contemporaneously but regulating the velocities in such a manner that the addition of the isopropylamine would be terminated in 20' while that of the sodium hydroxide would be terminated in 25' (velocities ratio of 1.25:1).

During the addition the temperature rose from +5° C to 52° C (at 20° C the brine has been discharged), while the pH reached a value of 10 at the end.

750 ml of water have been added and the mass has been cooled at 20° C and the resulting suspension has been filtered.

The thus obtained solid has been washed until elimination of the sodium chloride.

The product has been dried in oven for 10 hours at 100° C, thus obtaining 221 g of 2-chloro-4,6-bis- isopropylamino-s-triazine (propazine), with a yield, referred to the cyanuric chloride, of 96% and a purity higher than 99%.

EXAMPLE 12 (COMPARISON)

The test described in Example 1 has been repeated, without bringing the pH at 2-3 in the first step and without discharging the aqueous phase obtained after the addition of hydrochloric acid.

In particular, after obtaining in the frist step a pH value of 6-7, the mixture has been allowed to react for another 15' longer at about 20° C and thereafter the addition of the hydrochloric acid has not been performed, but 90 g of a 50 wt.% ethylamine aqueous solution and 138 g of a 30 wt.% sodium hydroxide aqueous solution have been directly added under vigorous stirring.

After carrying out the other operations described in Example 1, atrazine substantially in the same amounts and yields as in Example 1, has been obtained but with a purity equal to about 94%.

We claim:

1. In a method for the production of 2-chloro-s-triazine substituted in at least one of the positions 4,6 of the triazine ring with an amino group, by reaction in a water-organic liquid medium between cyanuric chloride and an amine in the presence of sodium hydroxide, the improvement which comprises:

feeding gradually, contemporaneously and separately an aqueous solution of a primary or secondary amine and an aqueous solution of sodium hydroxide into a reaction medium containing a solution of cyanuric chloride in an organic liquid immiscible or partially miscible with water, having a boiling point of from 60° to 130° C; adjusting the feed rate of the amine and sodium hydroxide solutions so as to feed per unit of time from 1.05 to 1.30 moles of amine for each mole of sodium hydroxide;

stopping the feeding of the amine solution when an amount of from 1 to 2 moles of amine per mole of cyanuric chloride has been added to the reaction medium;

stopping the feeding of the sodium hydroxide solution when an amount of sodium hydroxide moles equal to or slightly higher than the amount of amine moles fed in is reached in the reaction medium;

maintaining during the feeding period the temperature of the reaction medium at a value of from 5°-15° C to 60°-70° C; and recovering the resulting substituted 2-chloro-s-triazine from the reaction medium.

2. The method of claim 1, wherein two different amino groups are fixed in the positions 4 and 6 of the triazine ring by:

feeding contemporaneously and separately in a first reaction stage an aqueous solution of a first amine and an aqueous solution of sodium hydroxide into said reaction medium;

adjusting the feed rate of said first amine and sodium hydroxide solutions so as to feed per unit of time from 1.05 to 1.30 moles of said first amine for each mole of sodium hydroxide;

stopping the feeding of said first amine solution when an amount of 1 mole of amine per mole of cyanuric acid is reached in the reaction medium;

stopping the feeding of the sodium hydroxide solution when an amount of NaOH moles equal to or slightly higher than the amount of amine moles fed in is reached in the reaction medium;

maintaining during the feed period the temperature of the reaction medium at a value of from 5°-15° to 20°-25° C;

bringing the pH of the reaction medium to a value lower than 4 and recovering from said reaction medium the organic phase containing the resulting 2,4-dichloro-6-amino-s-triazine;

feeding contemporaneously and separately in a second reaction stage an aqueous solution of a second and different amine and an aqueous solution of sodium hydroxide into the said recovered organic phase;

adjusting the feed rate of said second amine and sodium hydroxide solutions so as to feed per unit of time from 1.05 to 1.30 moles of said second amine for each mole of sodium hydroxide;

stopping the feeding of said second amine solution when an amount of 1 mole of said second amine per mole of 2,4-dichloro-6-amino-s-triazine is reached in the reaction medium;

stopping the feeding of the sodium hydroxide solution when an amount of sodium hydroxide moles equal to or slightly higher than the amount of second amine moles fed in is reached in the reaction medium;

maintaining during the feed period the temperature of the reaction medium at a value of from 20°–25° C to 60°–70° C; and recovering from the reaction medium the resulting 2-chloro-s-triazine substituted in the positions 4 and 6 with two different amine groups.

3. The method of claim 2, wherein said pH of the reaction medium is brought to a value of from 2 to 3 at the end of said first reaction stage.

4. The method of claim 1, wherein said primary or secondary amine is selected in the group consisting of ethylamine, isopropylamine, tert-butylamine and diethylamine.

5. The method of claim 1, wherein the amount of water in said water-organic liquid medium does not exceed 50% by weight.

6. The method of claim 1, wherein said organic liquid is selected in the group consisting of toluene, chlorobenzene, carbon tetrachloride, methyl ethyl ketone, methyl propyl ketone and diethyl ketone.

7. The method of claim 1, wherein the feeding of the sodium hydroxide solution is stopped when reaching in the reaction medium an amount in moles of NaOH of from the amount of amine moles fed in to an excess of 5% with respect to the latter.

8. The method of claim 7, wherein said amount in moles of NaOH is in excess of from 2 to 4% with respect to the amount of amine moles, fed in.

9. The method of claim 1, wherein said reaction medium is maintained at the temperature reached at the end of said feeding period for a period of from 5 to 15 minutes.

10. The method of claim 1, wherein said substituted 2-chloro-s-triazine is recovered from the reaction medium by removing the organic liquid by azeotropic distillation with water and recovering said substituted 2-chloro-s-triazine suspended in the resulting residual solution.

11. The method of claim 1, wherein said substituted 2-chloro-s-triazine is recovered from the reaction medium by diluting the latter with water and separating the substituted 2-chloro-s-triazine suspended in the resulting solution.

12. The method of claim 1, wherein said production is a batch-wise production.

13. The method of claim 1, wherein said solution of cyanuric chloride contains all of the cyanuric chloride to be reacted.

14. The method of claim 1, wherein said substituted 2-chloro-s-triazine is 2-chloro-4,6-bis(ethylamino)-s-triazine or 2-chloro-4,6-bis(isopropylamino)-s-triazine.

15. The method of claim 2, wherein said 2-chloro-s-triazine substituted in the positions 4 and 6 with 2 different amino groups is 2-chloro-4-ethylamino-6-isopropyl amino -s-triazine, 2-chloro-4-ethyl amino-6-diethylamino-s-triazine or 2-chloro-4-ethylamino-6-tert-butylamino-s-triazine.

* * * * *